(12) United States Patent
Edelman

(10) Patent No.: US 8,257,777 B2
(45) Date of Patent: Sep. 4, 2012

(54) PHOTORESIST COATING TO APPLY A COATING TO SELECT AREAS OF A MEDICAL DEVICE

(75) Inventor: Peter Edelman, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1182 days.

(21) Appl. No.: 12/100,602

(22) Filed: Apr. 10, 2008

(65) Prior Publication Data

US 2008/0254297 A1 Oct. 16, 2008

Related U.S. Application Data

(60) Provisional application No. 60/923,016, filed on Apr. 11, 2007.

(51) Int. Cl.
*B05D 3/06* (2006.01)
*B05D 5/00* (2006.01)
*A61F 2/06* (2006.01)

(52) U.S. Cl. ....... 427/2.24; 427/2.1; 427/2.25; 427/256; 427/261; 427/273; 623/1.42; 623/1.43; 623/1.44; 623/1.46

(58) Field of Classification Search ............... 427/2.1, 427/2.24, 2.25, 256, 261, 264, 532, 551; 623/1.42–1.46
See application file for complete search history.

(56) References Cited

U.S. PATENT DOCUMENTS

| | | | |
|---|---|---|---|
| 4,869,714 A | | 9/1989 | Deininger |
| 5,084,311 A * | | 1/1992 | Liu et al. .................. 428/35.8 |
| 5,824,049 A | | 10/1998 | Ragheb et al. |
| 5,855,802 A * | | 1/1999 | Acciai et al. .................. 216/8 |
| 6,096,070 A | | 8/2000 | Ragheb et al. |
| 6,273,908 B1 * | | 8/2001 | Ndondo-Lay ............... 623/1.43 |
| 6,287,628 B1 * | | 9/2001 | Hossainy et al. ............. 427/2.3 |
| 6,506,437 B1 * | | 1/2003 | Harish et al. ................. 427/2.25 |
| 6,558,733 B1 * | | 5/2003 | Hossainy et al. ............. 427/2.24 |
| 6,758,859 B1 * | | 7/2004 | Dang et al. ................... 623/1.15 |
| 6,783,543 B2 * | | 8/2004 | Jang ............................ 623/1.15 |
| 7,575,593 B2 * | | 8/2009 | Rea et al. ..................... 623/1.42 |
| 2001/0035456 A1 * | | 11/2001 | Lennox ........................ 235/379 |
| 2002/0017503 A1 * | | 2/2002 | Banas et al. ................. 219/69.11 |
| 2003/0028243 A1 * | | 2/2003 | Bates et al. .................. 623/1.15 |
| 2004/0026359 A1 * | | 2/2004 | Dufresne et al. .................. 216/8 |
| 2004/0193257 A1 * | | 9/2004 | Wu et al. ...................... 623/1.46 |
| 2004/0236398 A1 * | | 11/2004 | Burgmeier et al. .......... 623/1.11 |
| 2005/0228491 A1 | | 10/2005 | Snyder et al. |
| 2006/0193886 A1 | | 8/2006 | Owens et al. |
| 2007/0031584 A1 | | 2/2007 | Roth |

FOREIGN PATENT DOCUMENTS

WO 03/023401 3/2003
WO WO 2004052947 A1 * 6/2004

OTHER PUBLICATIONS

International Search Report and Written Opinion, PCT/US2008/059849, Jul. 14, 2008.
Interrante, et al., "Chemistry of Advanced Material, an Overview," 1998, Wiley-VCH, pp. 99-141.
Wong, "Polymers for Electronic and Photonic Application," 1993, Academic Press, pp. 67-117.

\* cited by examiner

*Primary Examiner* — Timothy Meeks
*Assistant Examiner* — Cachet Sellman
(74) *Attorney, Agent, or Firm* — Kenyon & Kenyon LLP

(57) ABSTRACT

Methods and devices for coating a medical device, such as a stent, including the steps of coating the medical device with a photoresist polymeric coating, irradiating a portion of the medical device, optionally applying a post-exposure bake step, and removing all or a portion of the coating from the irradiated portion of the medical device, if a positive photoresist coating material is used, or from a portion of the medical device not exposed to the radiation, if a negative photoresist coating material is used. The photoresist polymeric coating may optionally include a drug.

10 Claims, 3 Drawing Sheets

PHOTORESIST COATING TO APPLY A COATING TO SELECT AREAS OF A MEDICAL DEVICE

CROSS-REFERENCE TO RELATED APPLICATIONS

This application claims priority to U.S. Provisional Application No. 60/923,016, filed Apr. 11, 2007, the disclosure of which is hereby incorporated by reference.

FIELD OF THE INVENTION

The present invention relates to methods and systems for coating a medical device, such as a stent.

BACKGROUND INFORMATION

Medical devices are used for a number of purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been achieved using medical implants, such as stents, which both support a lumen within a patient's body and place appropriate coatings containing absorbable therapeutic agents at the implant location. Examples of such medical devices that can be used for localized delivery of therapeutic agents include catheters, guide wires, balloons, valves, shunts, filters (e.g., vena cava filters), stents, stent grafts, vascular grafts, intraluminal paving systems, implants and other devices used in connection with drug-loaded polymer coatings. Such medical devices are implanted or otherwise utilized in body lumina and organs such as the coronary vasculature, peripheral vasculature, esophagus, trachea, colon, biliary tract, urinary tract, prostate, brain, and the like.

The process of applying a coating onto a medical device, such as a stent, may be accomplished by a number of methods including, for example, spray coating, spin-coating, dip coating, meniscus coating, gravure coating, ink jet printing, and electrostatic deposition. For certain applications only a specific portion, such as the outer or inner surface, of a medical device requires coating. For other applications, different portions of the medical device require coatings of different thicknesses. Given the often complex geometry of the medical device and the fluid nature of the coating it is difficult to tightly control the specific areas on the medical device that receive coating and the thicknesses of the coating. Therefore, there is a need for an improved method and device for coating medical devices that allows for greater control of the location and/or thickness of a coating application.

SUMMARY

The present invention concerns methods and apparatus for providing a coating on a structure. In an exemplary embodiment, the present invention is directed to a medical device, such as a stent, having a first portion coated with a photoresist polymeric coating and second uncoated portion.

In an exemplary embodiment of the present invention, the medical device is first coated with the photoresist polymeric coating and then a portion of the medical device, such as the inside surface or the outside surface, is irradiated. Next, the surface of the device is irradiated in selective locations depending on whether the resist is positive or negative and depending on where it is desired to have the coating located. Next, at least a portion of the medical device, e.g., including the photoresist coating, is optionally heated, e.g., put through a post-exposure baking process, if it is determined that such a process can improve the desired result, such as rendering a greater solubility difference between the insoluble portion and the soluble portion. Exemplary baking process are described in "Chemistry of Advanced Materials: An Overview (Chemistry of Advanced Materials)" by Leonard V. Interrante and Mark J. Hampden-Smith, Copyright 1998, Wiley-VCH, and "Polymers for Electronic & Photonic Application" by C. P. Wong, Copyright 1993, AT&T Bell Labs, Academic Press., both of which are herein incorporated in their entireties by reference thereto. Next, if a positive photoresist coating material is used, the entire thickness or only a fraction of the thickness of the coating formed by the coating material is removed from the irradiated portion of the medical device, or, if a negative photoresist coating material is used, the entire thickness or only a fraction of the thickness of the coating formed by the coating material is removed from a portion of the medical device not exposed to the radiation.

In an exemplary embodiment of the present invention, the photoresist polymeric coating may optionally include a drug.

In an exemplary embodiment of the present invention different portions of the medical device may be coated with different photoresist polymer coatings.

In an exemplary embodiment of the present invention, the body of the medical device may be coated with a photoresist polymeric coating varying in thickness along the body, i.e., a first portion of the photoresist polymeric coating may have a different thickness than a second portion of the coating.

In an exemplary embodiment of the present invention, the medical device may be a stent, catheter, guide wire, balloon, valve, filter, graft, suture, needle, intraluminal paving system, or any other medical device which may benefit from a controlled application of a coating.

A method for coating a medical device according to an exemplary embodiment of the present invention, includes the steps of:

a) applying a coating material, e.g., a photoresist polymeric coating material optionally including a drug, onto the medical device, the coating material adapted to become either more or less soluble, e.g., in a solvent, upon exposure to radiation;

b) irradiating a first portion of the coating material on the medical device so as to render the first portion of the coating material on the medical device either more or less soluble in the solvent than a second portion of the coating material;

c) optionally applying a baking process to at least a portion of the medical device; and d) removing coating material from the medical device from either (i) only one of the first and second portions, by, for example, exposing the coating material to a solvent in which only one of the first and second portions is soluble within an operative time frame, or (ii) from both of the first and second portions but from one more so than the other, by, for example, exposing for a predetermined amount of time the coating material to a solvent in which both the first and second portions are soluble but to a different degree.

In an exemplary embodiment of the present invention, the method for coating the medical device further includes the step of disposing a radiation source within the medical device and using said radiation source in step (b) above.

In an exemplary embodiment of the present invention, the medical device may be a stent and the coating material may include a positive photoresist polymer, i.e., a photoresist adapted to become more soluble upon irradiation by a predetermined radiation wavelength.

In an exemplary embodiment of the present invention, after irradiation in step (b) an entire thickness or a fraction of the thickness of a coating formed by the coating material may be removed from an inner surface of the stent in step (d). Alternatively, the coating material may be a negative photoresist polymer, i.e., a photoresist adapted to become less soluble upon radiation, and after irradiation the entire thickness or a fraction of the thickness of the coating formed by the coating material may be removed from only an outer surface of the medical device.

In an exemplary embodiment of the present invention, the radiation may be generated outside the medical device.

In an exemplary embodiment of the present invention, the medical device may be a stent and the coating material may include a negative photoresist polymer adapted to become less soluble upon irradiation by a predetermined radiation wavelength, and wherein after irradiation from outside the medical device, the entire thickness or a fraction of the thickness of a coating formed by the coating material may be removed from an inner surface of the stent in step (d). Alternatively, the entire thickness or only a fraction of the thickness of the coating formed by the coating material may be removed from only an outer surface of the medical device if a positive photoresist polymer adapted to become more soluble upon radiation is used.

In an exemplary embodiment of the present invention, the radiation may be applied to the coating material through a mask that is designed to allow radiation to only fall on predetermined portions of the medical device. The mask may be placed between the medical device and the radiation source.

In an exemplary embodiment of the present invention, the radiation may be applied to the coating material using a laser that is designed to allow radiation to only fall on predetermined portions of the medical device. The wavelength of the laser irradiation may be tuned to give optimal changes in solubility. The regions of the laser illumination may be placed in a controlled manner to precisely control the location where the coating is rendered either more or less soluble depending on whether the resist is a positive or a negative resist.

In an exemplary embodiment of the present invention, the thickness of the coating formed by the coating material may be controlled, for example, to assure a thinner layer at an end or edge of the stent. A feathered stent edge could minimize delamination by creating a more compliant interface, for example, on a high strain region of a stent, such as the inside of a hinge portion. A different coating thickness on different portions of the stent may be achieved by exposing different portions of the coated stent to radiation having a different wavelength and/or amplitude such that upon exposure to a solvent for a predetermined amount of time different amounts of coating material are removed from the differently treated portions of the stent. Alternatively, rather than varying the wavelength and/or amplitude of the radiation used, different photoresist coating materials may be used on different portions of the stent, which are removable at different rates upon exposure to a given solvent. In another exemplary embodiment, different coating thicknesses may be achieved by selectively exposing the different portions of a stent coated with a given photoresist coating material to different solvents or to a single solvent for different lengths of time.

BRIEF DESCRIPTION OF THE DRAWINGS

The present invention will become more fully understood from the detailed description given hereinbelow and the accompanying drawing, which are given by way of illustration only and wherein.

DETAILED DESCRIPTION

Figure 1A:
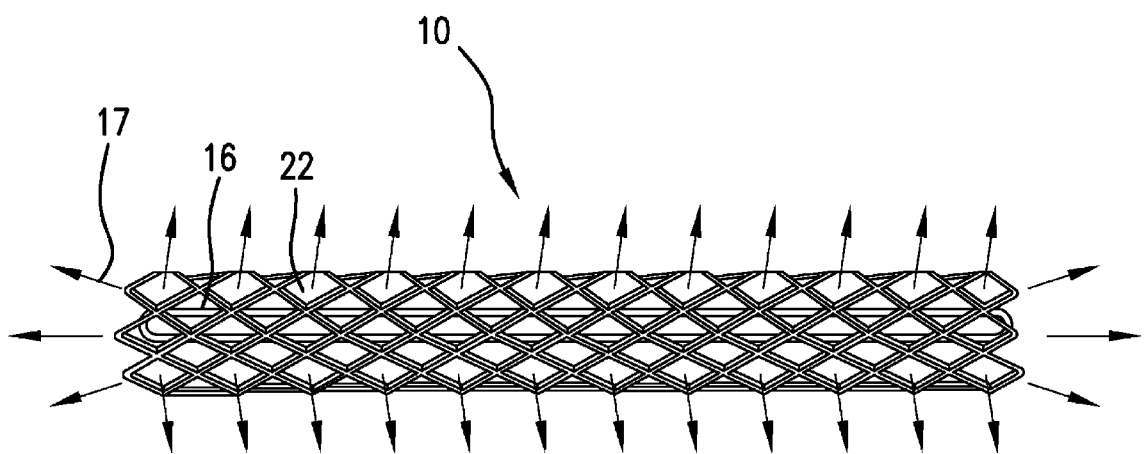
FIG. 1A is a schematic illustration of an exemplary system according to the present invention for coating a stent.
Figure 1B:
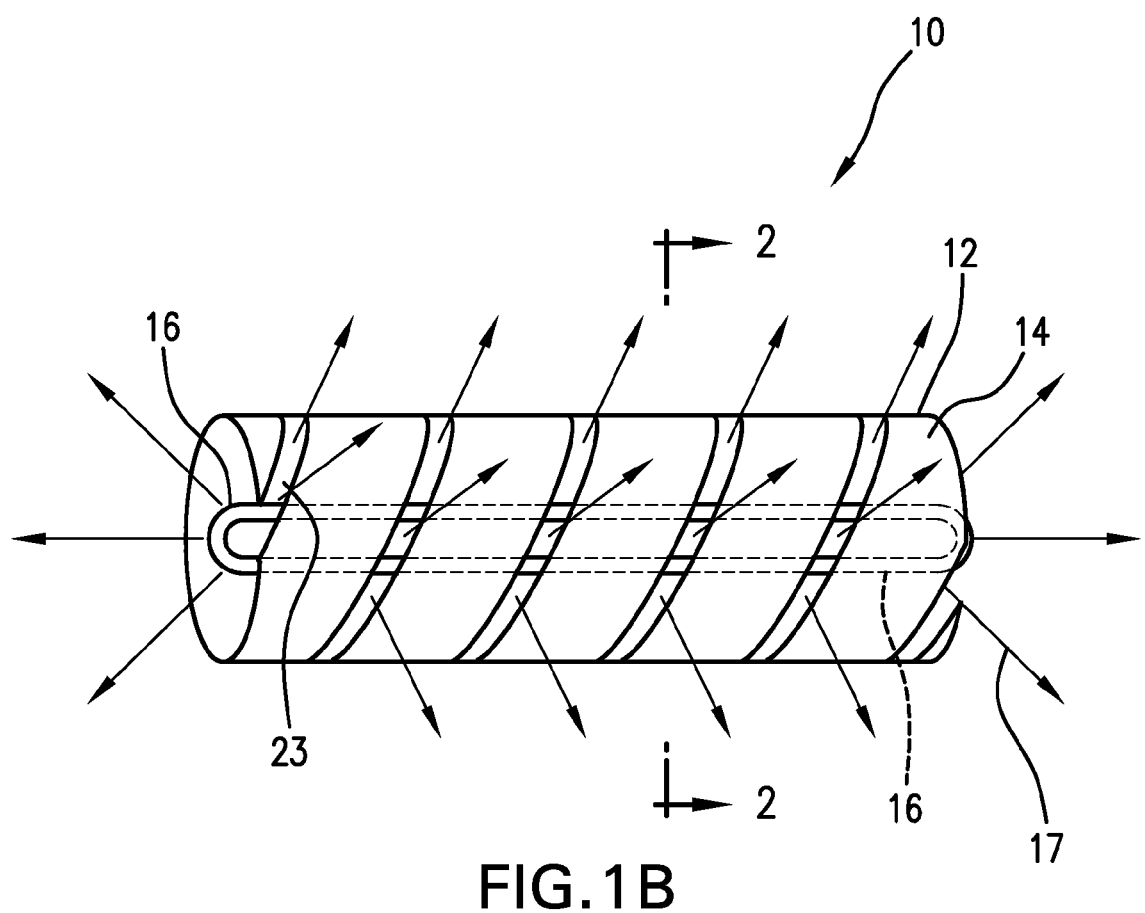
FIG. 1B is a schematic illustration of an exemplary system according to the present invention for coating another stent.

FIGS. 1A and 1B illustrate exemplary embodiments of a system 10 according to the present invention for coating a medical device, such as a stent 12. Stent 12 is coated with a coating material 14, such as a polymeric photoresist coating.

An example of a negative photoresist that is biocompatible would include a formulation containing an oligomer with acrylate reactive end groups. The middle portion of this oligomer with acrylate end groups can contain alternatively hydrophilic, non-thrombogenic components or hydrophobic non-thrombogenic components. An example of a hydrophilic non-thrombogenic composition would include materials such as oligoethyleneoxide or copolymers of phosphoryl choline. An example of more hydrophobic non-thrombogenic compositions would include an oligo-isobutylene material.

An example of a photocrosslinkable system based on photoacid generation is the system of a copolymer of hydroxyethyl methacrylate with methyl methacrylate. The hydroxl groups can be crosslinked using external crosslinkers and photoacid generators. An example of a photoinitiator for this system is Irgacure 261 from Ciba Specialty Chemicals, Irgacure 261 is $(\eta^6\text{-naphtalene})(\eta^5\text{-cyclopentadienyl})\text{iron(II)}$ hexafluorophosphate. The external crosslinker is tetramethoxymethyl glycoluril. Upon irradiation, O-alkylation occurs through the hydroxyl functionality.

Copolymers based on the structure of SU-8 are in the class of positive photoresists. The well known photoresist SU-8 has been known to be rendered more biocompatible by copolymerizing with more hydrophilic monomers. The stent 12 illustrated in FIG. 1A is tubular and has a pattern of cut-outs or openings 22, for example, cut or laser etched into the body of the stent 12. The stent illustrated in FIG. 1B is also tubular but has a different opening pattern 23. Stent 12 may have any other known configuration and opening pattern as well.

Figure 2:
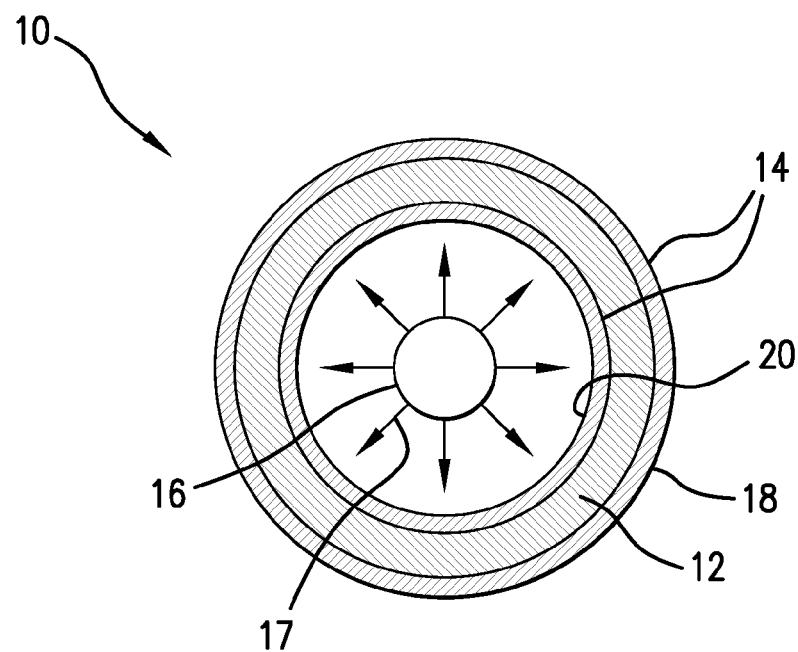
FIG. 2 is a transverse cross section of the stent illustrated in FIG. 1B taken along lines 2-2.

The coated stent 12 is disposed about a radiation source 16, such as a light. The radiation source 16 is turned on and caused to emit radiation 17 (shown as arrows) at a predetermined wavelength and amplitude which contacts an inner surface 20 of the stent 12 and passes through the openings 22 or cut-outs 23 in a body of the stent 10. FIG. 2 is a transverse cross section of the stent 12 taken along lines 2-2 in FIG. 1B. Given the positioning of the radiation source 16 within the stent 12, radiation 17 generated by the radiation source 16 does not contact an outer surface 18 of the stent 12.

The optimal wavelength of radiation depends on the photoaction spectrum of the photoactive molecules involved. In the case of a negative resist system using an acrylate end capped oligomer, a photoinitiator is employed in the formulation to initiate the reaction required to achieve insolubility. The photoinitiator is usually a free radical initiator, but can also be a hydrogen abstraction type. The choice of radiation wavelength is determined by the photoinitiator that is used. Different photoinitiators have different optimal wavelengths. It is important that the emission spectrum of the light source overlap with the absorption spectrum of the photoinitiator. For the free radical generating initiators, the preferred wavelengths are in the UV portion of the spectrum.

Figure 3:
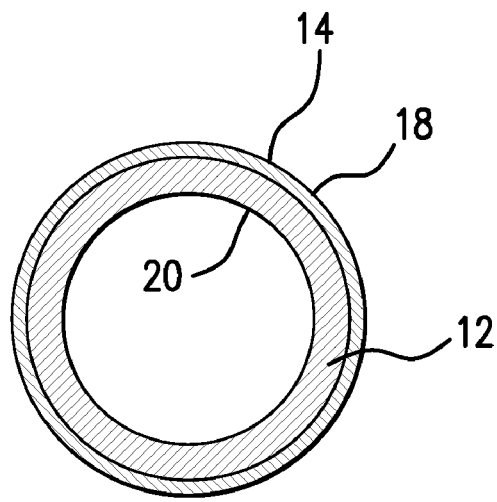
FIG. 3 is a transverse cross section of a stent having an outer coating according to the present invention.

In an exemplary embodiment of the present invention, a positive photoresist coating material 14 may be used such that coating material 14 on the inner surface 20 of the stent 12 exposed to radiation 17 is rendered more soluble than the coating material 14 on the outer surface 18 of the stent 12. This facilitates removal of an entire thickness or a fraction of the thickness of the coating material 14 from the inner surface 20, e.g., by washing off the stent 12, exposing the coating material 14 on the inner surface 20 to a solvent in which coating material 14 is soluble, etc., without removing coating material 14 on the outer surface 18 or removing less of the coating material on the outer surface 18, which has not been rendered more soluble by the radiation 17. FIG. 3 illustrates a transverse cross section of the stent 12 after the coating material 14 has been washed off the inner surface 20.

In an exemplary embodiment of the present invention, a negative photoresist coating material 14 may be employed, using the above-described apparatus, so as to retain coating material 14 only the inner surface 20 of the stent or to retain more coating material 14 on the inner surface 20 than on the outer surface 18.

Figure 4:
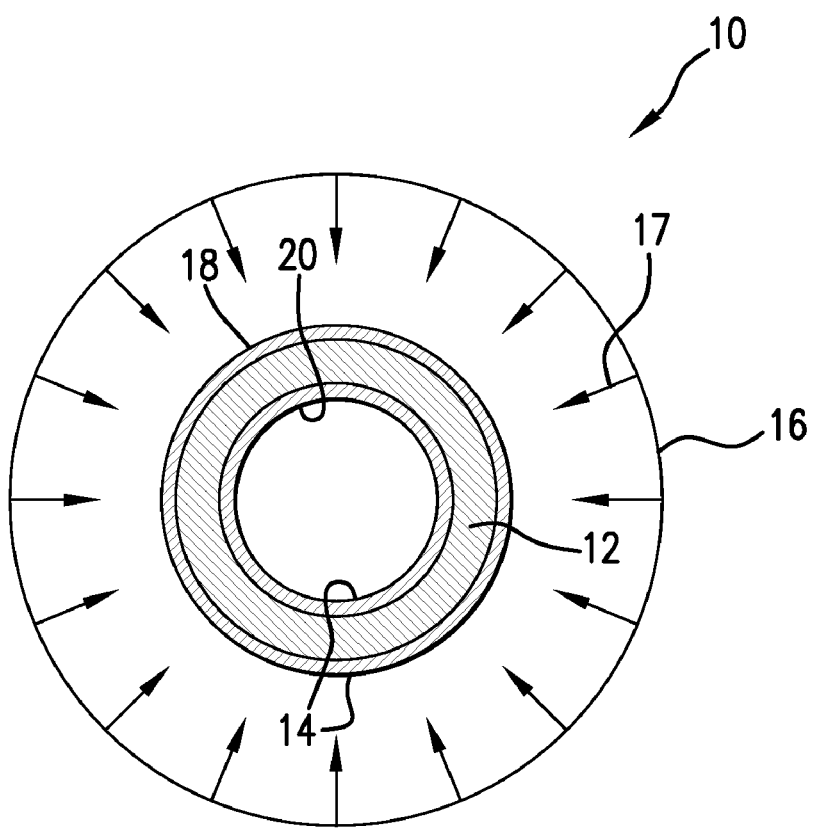
FIG. 4 is a transverse cross section of an exemplary system according to the present invention with the radiation source outside the stent.

In an exemplary embodiment of the present invention, the radiation source 16 may be positioned outside the stent 12 such that radiation 17 contacts only the outer surface 18 of the stent 12. For example, the radiation source 16 may be cylindrical or ring shaped and disposed about stent 12, as illustrated in FIG. 4.

A negative photoresist coating material 14 may be used such that coating material 14 on the outer surface 18 of the stent 12 exposed to radiation 17 is rendered less soluble than the coating material 14 on the inner surface 20 of the stent 12. This facilitates removal of an entire thickness or a fraction of the thickness of the coating material 14 from the inner surface 20, e.g., by washing off the stent 12, without removing coating material 14 on the outer surface 18 at all or with removing less coating material on the outer surface 18 than from the inner surface 20. The coating material 14 may be applied to stent 12 before or after formation of cut-outs 23 in stent 12. Further, openings 22 or cut-outs 23 may be closed with a filler while stent 12 is exposed to radiation 17 so as to prevent radiation 17 from contacting the coating material 14 on the inner surface 20. Alternatively, an opaque mandrel, sleeve, balloon or other blocking structure may be placed on the inside of the stent 12 to prevent radiation from contacting the coating material 14 on the inner surface 20. In the case of a balloon, the stent 12 may be placed on a deflated balloon, after which the balloon is expanded to contact and cover the inner surface 20.

In an exemplary embodiment of the present invention, a positive photoresist coating material 14 may be used, using the above-described apparatus including the radiation source outside the stent 12, so as to coat only the inner surface 20 of the stent.

In an exemplary embodiment of the present invention, after exposure to radiation 17 but prior to removal of the coating material 14, at least a portion of the stent 12, e.g., including the coating material 14, is optionally heated, e.g., put through a post-exposure baking process, so as to achieve a greater solubility difference between the insoluble portion and the soluble portion of the coating material 14. Exemplary baking processes are described in "Chemistry of Advanced Materials: An Overview (Chemistry of Advanced Materials)" by Leonard V. Interrante and Mark J. Hampden-Smith, Copyright 1998, Wiley—VCH, and "Polymers for Electronic & Photonic Application" by C. P. Wong, Copyright 1993, AT&T Bell Labs, Academic Press., both of which are herein incorporated in their entireties by reference thereto.

In an exemplary embodiment of the present invention, the baking temperature may be between 40° C. to 150° C. In another exemplary embodiment, the baking temperature may be between 50° C. to 100° C. In another exemplary embodiment, the baking temperature may be between 60° C. to 90° C. The baking temperature may be selected to achieve the optimal solubility difference without deleteriously affecting any pharmacological agent which may be incorporated.

In an exemplary embodiment of the present invention, a surface treatment to the bare stent 12, e.g., silanization or a conformal layer of parylene, may be applied so as to improve adhesion.

In an exemplary embodiment of the present invention, different portions of the stent 12 may be coated with different coating thicknesses. For example, different portions of the inner surface 20 and/or outer surface 18 may have different thicknesses, for example, to achieve a feathered stent edge. Alternatively, the inner surface 20 and the outer surface 18 may have different coating thicknesses. For example, a second radiation source, delivering a different wavelength and/or amplitude radiation than that delivered by the first radiation source 16, may be disposed about the stent 12 of FIGS. 1A and 1B and used together with the first radiation source 16 to deliver radiation to the stent 12. Upon exposure of the coated stent 12 to a solvent for a predetermined amount of time a different percentage of the coating thickness will be removed on the inner surface 20 and the outer surface 18 of the stent 12, as a result of the different radiation that the coating material on these surfaces was exposed to, yielding a different coating thickness on these surfaces.

In an exemplary embodiment of the present invention, different thicknesses may be applied to different portions of the stent 12, e.g., to control the amount of drug delivered. For example, in the region around a bifurcation, there may be some advantage to have more or less drug at the site of the bifurcation.

In an exemplary embodiment of the present invention, different formulations can be layered on the stent 12. The formulations may differ, e.g., by the inclusion of different pharmacological agents or by having different ratios of excipients, to control, in layer fashion, the release rate. A rate limiting outer layer may also be applied over the outer most drug containing layer.

In an exemplary embodiment of the present invention, different drugs can be applied at different locations on the stent 12. Using, for example, a laser photo-initiation method for curing the polymer in place on the stent 12, the stent 12 can be dipped in baths of differing formulations. For example, a first drug may be formulated into the coating every where on the stent 12 except a second region where it may be advantageous to have an alternate drug. After the first drug is incorporated into a coating on the stent 12, the stent 12 may be dipped into a second formulation containing the same or a different excipient formulation, with a different drug. The different drug may be more advantageous for treating a different disease in a different anatomical portion in contact with the stent 12.

Coating material 14 may be applied to stent 10 using any type of delivery technique. For example, the coating material 14 may be sprayed onto the stent 12 and/or the stent 12 may be dipped into a bath of the coating material 14. The coating material 14 may also be delivered using electrostatic deposition, as described, for example, in U.S. Pat. Nos. 5,824,049 and 6,096,070 to Ragheb et al., herein incorporated in their entirety by reference thereto. Alternatively, the coating material 12 may be delivered using a gravity flow process in which a container is placed over stent 12 and a controlled amount of coating material is released onto the stent 12, for example, by tipping the container or opening a container door.

A mask may be placed between the radiation source 16 and the stent 12 so as to expose only selected portions on, for example, the outer surface 18 of stent 12 to radiation 17. In one exemplary embodiment, the mask may have a cylindrical shape and have a specific pattern of cut-outs. The mask may also take on other shapes depending on the desired coating pattern. Further, a laser or other source of highly concentrated radiation source may be scanned across a surface of the stent 12 so as to map out a desired coating pattern on the stent 12.

Non-limiting examples of medical devices according to the present invention include catheters, guide wires, balloons, filters (e.g., vena cava filters), stents, stent grafts, vascular grafts, intraluminal paving systems, needles, sutures, implants and other devices used in connection with coatings, e.g., drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

The drug optionally included in the coating material 14 may be any pharmaceutically acceptable therapeutic agents such as non-genetic therapeutic agents, biomolecules, small molecules, or cells. Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl) ethyleneglycol-N,N,N',N'-tetraacetic acid and mixtures thereof, antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; angiotensin converting enzyme (ACE) inhibitors; beta-blockers; bAR kinase (bARKct) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin$^-$) cells including Lin$^-$CD34$^-$, Lin$^-$CD34$^+$, Lin$^-$cKit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

The polymers included in the coating material 14 may be biodegradable or non-biodegradable. Further, portions of the stent 12 may be coated with polymers not necessarily suitable as negative or positive resist polymers. Non-limiting examples of such non-biodegradable polymers include polystrene; polyisobutylene copolymers and styrene-isobutylene block copolymers such as styrene-isobutylene-styrene tri-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of biodegradable polymers not necessarily suitable as negative or positive resist polymers which may also be applied to portions of the stent 12 include poly($\beta$-hydroxy acids), poly($\alpha$-hydroxy acids), including, but not limited to, polylactic acid, polyglycolic acid and copolymers and mixtures thereof such as poly(L-lactic acid) (PLLA), poly(D,L,-lactide), poly(lactic acid-co-glycolic acid), 50/50 (DL-lactide-co-glycolide); polyanhydrides including maleic anhydride polymers; polyorthoesters; polyamino acids; polyethylene oxide; polyphosphazenes; polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Any of the above mentioned therapeutic agents may be incorporated into a polymeric coating on a medical device, such as stent 12, or applied onto a polymeric coating on the medical device. More specifically, the therapeutic agent may be added to the coating material mixture or may be applied as a separate layer over the applied coating mixture. The therapeutic agent may be separately applied, for example, via spraying, to the medical device.

The coating material 14 used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

Solvents may also be utilized in any order. For example, an initial polymer/solvent mixture can be formed and then the drug added to the polymer/solvent mixture. Alternatively, the polymer, solvent, and drug can be added simultaneously to form a mixture. Furthermore, multiple types of drug, polymers, and/or solvents may be utilized.

The stent 12 may also contain a radio-opacifying agent within its structure to facilitate viewing the stent 12 during insertion and at any point while the device is implanted. Non-limiting examples of radio-opacifying agents are bismuth subcarbonate, bismuth oxychloride, bismuth trioxide, barium sulfate, tungsten, and mixtures thereof.

The foregoing description and example have been set forth merely to illustrate the invention and are not intended as being limiting. Each of the disclosed aspects and embodiments of the present invention may be considered individually or in combination with other aspects, embodiments, and variations of the invention. None of the steps of the methods of the present invention are confined to any particular order of performance. Modifications of the disclosed embodiments incorporating the spirit and substance of the invention are within the scope of the present invention.

What is claimed is:

1. A method for coating a stent with a coating material comprising the steps of:
    a) applying a coating material including a drug onto the stent in such a manner that the coating material is on both an inner surface and an outer surface of the stent, the coating material adapted to become one of more and less soluble in a solvent upon exposure to radiation outside the solvent;
    b) irradiating a first portion of the coating material on the stent so as to render the first portion of the coating material on the stent one of more and less soluble in the solvent than a second portion; and
    c) exposing the coating material on at least the inner surface to the solvent so as to achieve one of:
        (i) removal of at least some of the irradiated first portion of the coating material and retaining the second portion of the coating material; and
        (ii) removal of at least some of the second portion of the coating material and retaining the irradiated first portion of the coating material.

2. The method according to claim 1, wherein the coating material comprises a photoresist polymer.

3. The method according to claim 1, further comprising the step of disposing a radiation source within the stent and using said radiation source for irradiation in step (b).

4. The method according to claim 3, wherein the coating material comprises a photoresist polymer adapted to become more soluble upon irradiation by a predetermined radiation wavelength, and wherein after irradiation in step (b) the coating material is removed from an inner surface of the stent in step (c).

5. The method according to claim 1, wherein radiation is generated outside the stent in step (b).

6. The method according to claim 5, wherein the coating material comprises a photoresist polymer adapted to become less soluble upon irradiation by a predetermined radiation wavelength, and wherein after irradiation in step (b) the coating material is removed from an inner surface of the stent in step (c).

7. The method according to claim 1, further comprising heating at least a portion of the stent after irradiating the stent in step (b).

8. The method according to claim 1, wherein the step of exposing the coating material to the solvent is performed for a predetermined period.

9. The method of claim 1, wherein the step of exposing the coating material to the solvent removes at least some of the coating material on the inner surface of the stent but the coating material on the outer surface of the stent is retained.

10. The method of claim 1, wherein the step of exposing the coating material to the solvent removes at least some of the coating material on the outer surface of the stent but the coating material on the inner surface of the stent is retained.

* * * * *